(12) United States Patent
Myles (10) Patent No.: US 12,220,523 B2
(45) Date of Patent: Feb. 11, 2025

(54) ELECTRONIC SMOKING DEVICE

(71) Applicant: Fontem Holdings 1 B.V., Amsterdam (NL)

(72) Inventor: Christopher Myles, San Jose, CA (US)

(73) Assignee: Fontem Ventures B.V., Amsterdam (NL)

( * ) Notice: Subject to any disclaimer, the term of this patent is extended or adjusted under 35 U.S.C. 154(b) by 740 days.

(21) Appl. No.: 16/103,918

(22) Filed: Aug. 14, 2018

(65) Prior Publication Data

US 2020/0054070 A1 Feb. 20, 2020

(51) Int. Cl.
*A24F 40/40* (2020.01)
*A61M 11/04* (2006.01)
*A24F 40/10* (2020.01)

(52) U.S. Cl.
CPC ........... *A61M 11/042* (2014.02); *A24F 40/40* (2020.01); *A24F 40/10* (2020.01)

(58) Field of Classification Search
CPC .......... A24F 40/10; A24F 40/30; A24F 40/40; A24F 40/42; A24F 40/48; A24F 47/008
See application file for complete search history.

(56) References Cited

U.S. PATENT DOCUMENTS

| | | | |
|---|---|---|---|
| 9,402,422 B2 | 8/2016 | Shenkal | |
| 9,413,180 B2 * | 8/2016 | Liu | H02J 7/00 |
| 9,999,245 B1 | 1/2018 | Zhu | |
| 2013/0333711 A1 * | 12/2013 | Liu | A24F 40/60 |
| | | | 131/329 |
| 2015/0296888 A1 | 10/2015 | Liu | |
| 2016/0150821 A1 * | 6/2016 | Liu | A24F 40/485 |
| | | | 131/329 |
| 2016/0235119 A1 * | 8/2016 | Liu | A24F 40/95 |
| 2016/0262449 A1 * | 9/2016 | Liu | A24D 1/02 |
| 2016/0353805 A1 * | 12/2016 | Hawes | A24F 47/004 |
| 2017/0259170 A1 * | 9/2017 | Bowen | A24F 40/60 |
| 2017/0281883 A1 * | 10/2017 | Li | A61M 15/0001 |
| 2018/0154103 A1 * | 6/2018 | Davis | A61M 15/0065 |
| 2018/0160732 A1 * | 6/2018 | Bless | A24F 40/30 |
| 2019/0200673 A1 * | 7/2019 | Bless | A24F 40/10 |
| 2020/0023155 A1 * | 1/2020 | Takehara | C25B 1/04 |
| 2020/0245685 A1 * | 8/2020 | Bostock | A24F 40/485 |
| 2021/0112879 A1 * | 4/2021 | Antonopoulos | H01R 39/64 |

FOREIGN PATENT DOCUMENTS

| | | |
|---|---|---|
| CN | 201403497 Y | 2/2010 |
| DE | 202014008768 U1 | 11/2014 |
| EP | 2575938 B1 | 7/2014 |
| EP | 3103356 A1 | 12/2016 |
| EP | 3158880 A1 | 4/2017 |
| WO | 2015054885 A1 | 4/2015 |
| WO | 2017102686 A1 | 6/2017 |
| WO | 2018032427 A1 | 2/2018 |

* cited by examiner

*Primary Examiner* — Katherine A Will
(74) *Attorney, Agent, or Firm* — Dykema Gossett PLLC (57) ABSTRACT

Various embodiments of the present disclosure are directed to customization of various physical attributes of an e-cigarette to a user's preference(s).

15 Claims, 3 Drawing Sheets

ELECTRONIC SMOKING DEVICE

FIELD OF INVENTION

The present invention relates generally to electronic smoking devices and in particular electronic cigarettes.

BACKGROUND OF THE INVENTION

An electronic smoking device, such as an electronic cigarette (e-cigarette), typically has a housing accommodating an electric power source (e.g., a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an air flow pattern through the device). The airflow sensor indicates or signals the puff to the control electronics to power up the device and generate vapor. In other e-cigarettes, a switch is used to power up the e-cigarette to generate a puff of vapor.

BRIEF SUMMARY

Various embodiments of the present disclosure are directed to customization of various physical attributes of an e-cigarette to a user's preference(s).

Aspects of the present disclosure are directed to an electronic smoking device including a power supply portion, and an atomizer/liquid reservoir portion. The atomizer/liquid reservoir portion is removeably coupled to the power supply portion. The atomizer/liquid reservoir portion may freely rotate about a longitudinal axis of the electronic smoking device, relative to the power supply portion. In some implementations, the atomizer/liquid reservoir portion may freely rotate about the longitudinal axis in response to a user input. The power supply portion may include, in some embodiments, controller circuitry with indicator lights. The controller circuitry is rotatably coupled to the atomizer/liquid reservoir portion, and rotates in response to a rotational input on the atomizer/liquid reservoir portion. The controller circuitry may further facilitate maintained visibility of the indicator lights by a user following the rotational input on the atomizer/liquid reservoir portion. In yet further more specific embodiments, the power supply portion further includes a communication port communicatively coupled to the controller circuitry. The communication port is rotatable about the longitudinal axis in response to the rotational input on the atomizer/liquid reservoir portion.

In some implementations of an electronic smoking device, the atomizer/liquid reservoir portion includes a nozzle, and the atomizer/liquid reservoir portion facilitates rotational alignment between the nozzle and a mouth of a user. The rotation of the atomizer/liquid reservoir portion, relative to the power supply portion, may be limited to a range between 90 and 180 degrees.

Various embodiments of the present disclosure are directed to a power supply portion of an electronic cigarette including a housing, a power supply situated within the housing, and controller circuitry situated within the housing and electrically coupled to the power supply. The controller circuitry rotates, about a longitudinal axis, relative to the housing in response to a rotational input on an atomizer/liquid reservoir portion when coupled to the power supply portion. In some implementations, the housing includes a transparent window, the controller circuitry includes one or more indicator lights, and the controller circuitry facilitates maintained visibility of the indicator lights by rotating in response to the rotational input of the atomizer/liquid reservoir portion. In yet other implementations, the controller circuitry, in response to the rotational input on the atomizer/liquid reservoir portion rotatably coupled to the power supply portion, facilitates maintained user visibility of the indicator lights through the transparent window by rotating. The power supply portion may further include a communication port communicatively coupled to the controller circuitry and which rotates with the controller circuitry about the longitudinal axis. In various implementations of the power supply portion discussed above, the rotation of the controller circuitry, relative to the housing, may be limited to 90 degrees.

Aspects of the present disclosure are also directed to methods of reconfiguring an electronic cigarette. The method including: applying a torque along a longitudinal axis of an atomizer/liquid reservoir portion of the electronic cigarette, translating the torque on the atomizer/liquid reservoir portion to controller circuitry housed within a power supply portion of the electronic cigarette, the controller circuitry rotatably coupled to the atomizer/liquid reservoir portion, and rotating the controller circuitry, in response to the translated torque on the controller circuitry. The step of rotating the controller circuitry may maintain user visibility of indicator lights on the controller circuitry. The indicator lights may be visible through a transparent window in the power supply portion that extends at least partially about a circumference of the power supply portion. In various implementations, the step of rotating the controller circuitry maintains rotational alignment of a communication port communicatively coupled to the controller circuitry and the atomizer/liquid reservoir portion. The method may further include limiting the rotation of the controller circuitry by discontinuing the translation of torque onto the controller circuitry once the rotation of the controller circuitry reaches 90 degrees.

Some method of reconfiguring an electronic cigarette, consistent with the present disclosure, may further include the step of rotating a communication port about the longitudinal axis. The communication port extending out of a window in the power supply portion which extends at least partially about a circumference of the power supply portion.

The characteristics, features and advantages of this invention and the manner in which they are obtained as described above, will become more apparent and be more clearly understood in connection with the following description of exemplary embodiments, which are explained with reference to the accompanying drawings.

The above discussion/summary is not intended to describe each embodiment or every implementation of the present disclosure. The figures and detailed description that follow also exemplify various embodiments.

BRIEF DESCRIPTION OF THE DRAWINGS

In the drawings, the same element numbers indicate the same elements in each of the views. Various example embodiments may be more completely understood in consideration of the following detailed description in connection with the accompanying drawings, in which.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DESCRIPTION OF THE PREFERRED EMBODIMENTS

Various embodiments of the present disclosure are directed to customization of various physical attributes of an e-cigarette to a user's preference(s).

Aspects of the present disclosure are directed toward an e-cigarette including disposable and non-disposable portions. In such embodiments, the disposable portion includes a cartomizer, heating coil, and mouthpiece. The non-disposable portion includes a power source, and electronic circuitry to drive the heating coil. When the disposable and non-disposable portions are coupled to one another, the disposable portion may be rotated to facilitate a user desired orientation of the mouthpiece relative to the non-disposable portion.

In further embodiments of the present disclosure, rotation of a disposable portion may cause rotation of electronic circuitry within a non-disposable portion about a longitudinal axis of the disposable portion. The electronic circuitry may include light emitting diodes ("LED") indicators, that when rotated about the longitudinal axis, facilitate visibility of the LED indicators from different sides of the non-disposable portion. Similarly, a Universal Serial Bus ("USB") port (or other charging/communication port which may facilitate the use of one or more communication protocols), communicatively coupled to the electronic circuitry, may be rotated about the longitudinal axis of the disposable portion to facilitate USB port access on two or more sides of the non-disposable portion.

Some embodiments of an electronic cigarette, consistent with the present disclosure, may include mechanical features to limit the rotation of the disposable and non-disposable portions of the e-cigarette relative to one another. Moreover, some additional mechanical features may be directed toward managing the wires which extend between an electronic circuitry and a battery (of the non-disposable portion) to prevent damage to the lead wires themselves, or the contact points between the lead wires, and electronic circuitry/battery due to rotation of the electronic circuitry relative to the battery.

In some specific embodiments of the present disclosure, an electronic cigarette is disclosed including disposable (e.g., atomizer/liquid reservoir portion) and non-disposable portions (e.g., power supply portion). The power supply portions may include a battery and controller circuitry communicatively coupled thereto. The controller circuitry may include a single circuit board with a mass air flow sensor, indicator LEDs, and charging circuitry for the battery. The LEDs may be positioned on the circuit board to align with a clear window in a housing of the non-disposable portion. Upon coupling the disposable portion to the non-disposable portion, the disposable portions may be rotated relative to the non-disposable portion of the e-cigarette along a longitudinal axis. Rotation of the disposable portion may be (in) directly coupled to the controller circuitry which rotates in kind. As a result, the LED indicators are rotated about the longitudinal axis to maintain user visibility regardless of the non-disposable portion's rotational angle relative to the user. That is, the user may utilize the e-cigarette in a way most comfortable to them for a particular situation. As discussed in more detail below, managing lead wires extending from the controller circuitry to, for example, a battery may be desirable to prevent unintentional decoupling of the lead wires to contact pads on the controller circuitry; for example, in response to excessive rotation of the disposable portion of the e-cigarette. In further embodiments, a communication port communicatively coupled to the controller circuitry may be rotatable (along with the controller circuitry) about the longitudinal axis. The communication port being accessible by the user on an external surface of the non-disposable portion.

Figure 1:
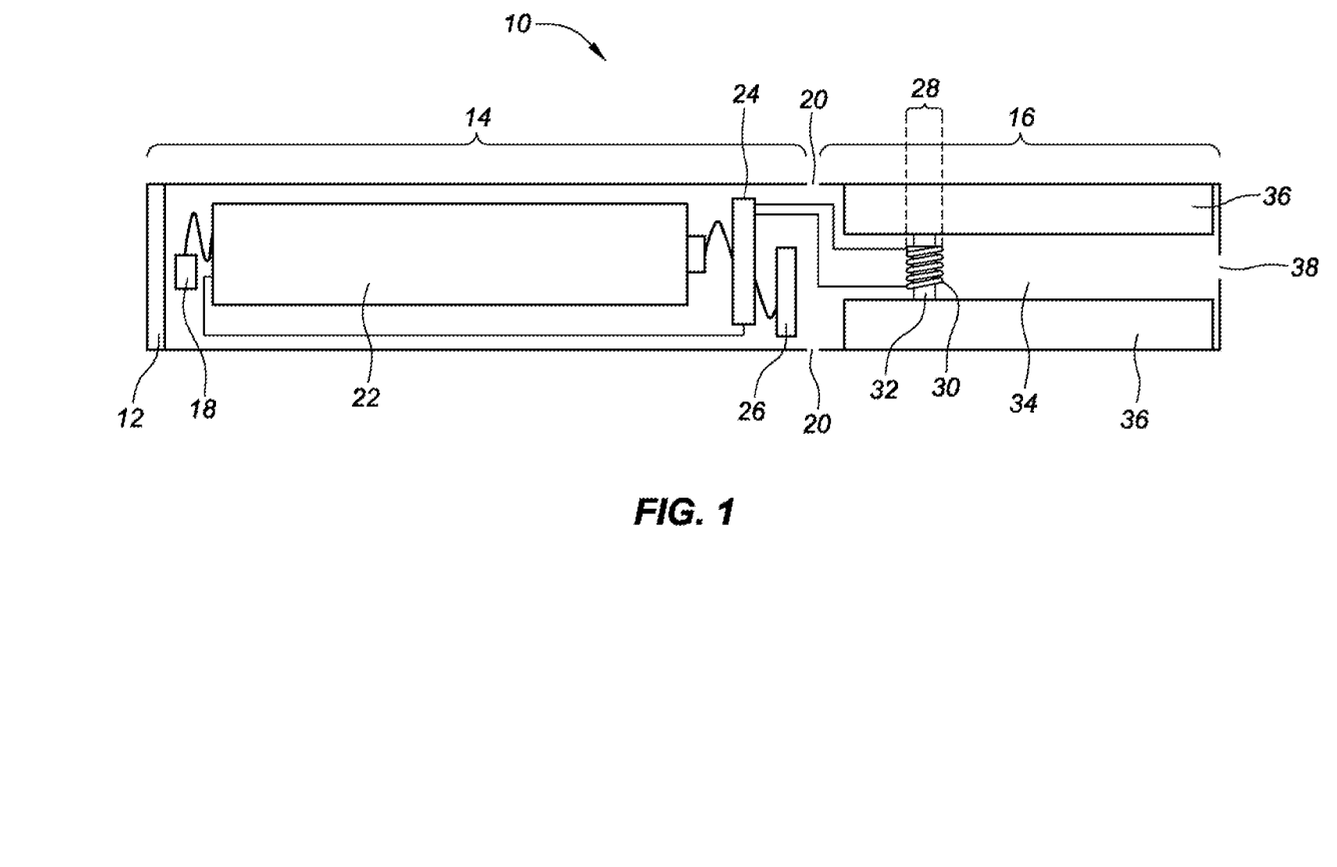
FIG. 1 is a schematic cross-sectional illustration of an e-cigarette, consistent with various embodiments of the present disclosure.

Throughout the following, an electronic smoking device will be exemplarily described with reference to an e-cigarette. As is shown in FIG. 1, an e-cigarette 10 typically has a housing comprising a cylindrical hollow tube having an end cap 12. The cylindrical hollow tube may be a single-piece or a multiple-piece tube. In FIG. 1, the cylindrical hollow tube is shown as a two-piece structure having a power supply portion 14 and an atomizer/liquid reservoir portion 16. Together the power supply portion 14 and the atomizer/liquid reservoir portion 16 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 14 and atomizer/liquid reservoir portion 16 are typically made of metal (e.g., steel or aluminum, or of hardwearing plastic) and act together with the end cap 12 to provide a housing to contain the components of the e-cigarette 10. The power supply portion 14 and the atomizer/liquid reservoir portion 16 may be configured to fit together by, for example, a friction push fit, a snap fit, a bayonet attachment, a magnetic fit, or screw threads. The end cap 12 is provided at the front end of the power supply portion 14. The end cap 12 may be made from translucent plastic or other translucent material to allow a light-emitting diode (LED) 18 positioned near the end cap to emit light through the end cap. Alternatively, the end cap may be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 14 and the atomizer/liquid reservoir portion 16. FIG. 1 shows a pair of air inlets 20 provided at the intersection between the power supply portion 14 and the atomizer/liquid reservoir portion 16.

A power supply, preferably a battery 22, the LED 18, control electronics 24 and, optionally, an airflow sensor 26 are provided within the cylindrical hollow tube power supply portion 14. The battery 22 is electrically connected to the control electronics 24, which are electrically connected to the LED 18 and the airflow sensor 26. In this example, the LED 18 is at the front end of the power supply portion 14, adjacent to the end cap 12; and the control electronics 24 and airflow sensor 26 are provided in the central cavity at the other end of the battery 22 adjacent the atomizer/liquid reservoir portion 16.

The airflow sensor 26 acts as a puff detector, detecting a user puffing or sucking on the atomizer/liquid reservoir portion 16 of the e-cigarette 10. The airflow sensor 26 can be any suitable sensor for detecting changes in airflow or air pressure, such as a microphone switch including a deformable membrane which is caused to move by variations in air pressure. Alternatively, the sensor may be, for example, a Hall element or an electro-mechanical sensor.

The control electronics 24 are also connected to an atomizer 28. In the example shown, the atomizer 28 includes a heating coil 30 which is wrapped around a wick 32 extending across a central passage 34 of the atomizer/liquid reservoir portion 16. The central passage 34 may, for example, be defined by one or more walls of the liquid reservoir and/or one or more walls of the atomizer/liquid reservoir portion 16 of the e-cigarette 10. The coil 30 may be positioned anywhere in the atomizer 28 and may be transverse or parallel to a longitudinal axis of a cylindrical liquid reservoir 36. The wick 32 and heating coil 30 do not completely block the central passage 34. Rather an air gap is provided on either side of the heating coil 30 enabling air to flow past the heating coil 30 and the wick 32. The atomizer may alternatively use other forms of heating elements, such as ceramic heaters, or fiber or mesh material heaters. Nonresistance heating elements such as sonic, piezo, and jet spray may also be used in the atomizer in place of the heating coil.

The central passage 34 is surrounded by the cylindrical liquid reservoir 36 with the ends of the wick 32 abutting or extending into the liquid reservoir 36. The wick 32 may be a porous material such as a bundle of fiberglass fibers or cotton or bamboo yarn, with liquid in the liquid reservoir 36 drawn by capillary action from the ends of the wick 32 towards the central portion of the wick 32 encircled by the heating coil 30.

The liquid reservoir 36 may alternatively include wadding (not shown in FIG. 1) soaked in liquid which encircles the central passage 34 with the ends of the wick 32 abutting the wadding. In other embodiments, the liquid reservoir may comprise a toroidal cavity arranged to be filled with liquid and with the ends of the wick 32 extending into the toroidal cavity.

An air inhalation port 38 is provided at the back end of the atomizer/liquid reservoir portion 16 remote from the end cap 12. The inhalation port 38 may be formed from the cylindrical hollow tube atomizer/liquid reservoir portion 16 or may be formed in an end cap.

In use, a user sucks on the e-cigarette 10. This causes air to be drawn into the e-cigarette 10 via one or more air inlets, such as air inlets 20, and to be drawn through the central passage 34 towards the air inhalation port 38. The change in air pressure which arises is detected by the airflow sensor 26, which generates an electrical signal that is passed to the control electronics 24. In response to the signal, the control electronics 24 activate the heating coil 30, which causes liquid present in the wick 32 to be vaporized creating an aerosol (which may comprise gaseous and liquid components) within the central passage 34. As the user continues to suck on the e-cigarette 10, this aerosol is drawn through the central passage 34 and inhaled by the user. At the same time, the control electronics 24 also activate the LED 18 causing the LED 18 to light up, which is visible via the translucent end cap 12. Activation of the LED may mimic the appearance of a glowing ember at the end of a conventional cigarette. As liquid present in the wick 32 is converted into an aerosol, more liquid is drawn into the wick 32 from the liquid reservoir 36 by capillary action and thus is available to be converted into an aerosol through subsequent activation of the heating coil 30.

Some e-cigarettes are intended to be disposable and the electric power in the battery 22 is intended to be sufficient to vaporize the liquid contained within the liquid reservoir 36, after which the e-cigarette 10 is thrown away. In other embodiments, the battery 22 is rechargeable and the liquid reservoir 36 is refillable. In the cases where the liquid reservoir 36 is a toroidal cavity, this may be achieved by refilling the liquid reservoir 36 via a refill port (not shown in FIG. 1). In other embodiments, the atomizer/liquid reservoir portion 16 of the e-cigarette 10 is detachable from the power supply portion 14 and a new atomizer/liquid reservoir portion 16 can be fitted with a new liquid reservoir 36 thereby replenishing the supply of liquid. In some cases, replacing the liquid reservoir 36 may involve replacement of the heating coil 30 and the wick 32 along with the replacement of the liquid reservoir 36. A replaceable unit comprising the atomizer 28 and the liquid reservoir 36 may be referred to as a cartomizer.

The liquid reservoir may be in the form of a cartridge (not shown in FIG. 1) defining a passage (or multiple passages) through which a user inhales aerosol. In other embodiments, the aerosol may flow around the exterior of the cartridge to the air inhalation port 38.

Of course, in addition to the above description of the structure and function of a typical e-cigarette 10, variations also exist. For example, the LED 18 may be omitted. The airflow sensor 26 may be placed, for example, adjacent to the end cap 12 rather than in the middle of the e-cigarette. The airflow sensor 26 may be replaced by, or supplemented with, a switch which enables a user to activate the e-cigarette manually rather than in response to the detection of a change in air flow or air pressure.

Different types of atomizers may be used. Thus, for example, the atomizer may have a heating coil in a cavity in the interior of a porous body soaked in liquid. In this design, aerosol is generated by evaporating the liquid within the porous body either by activation of the coil heating the porous body or alternatively by the heated air passing over or through the porous body. Alternatively, the atomizer may use a piezoelectric atomizer to create an aerosol either in combination or in the absence of a heater.

Figure 2:
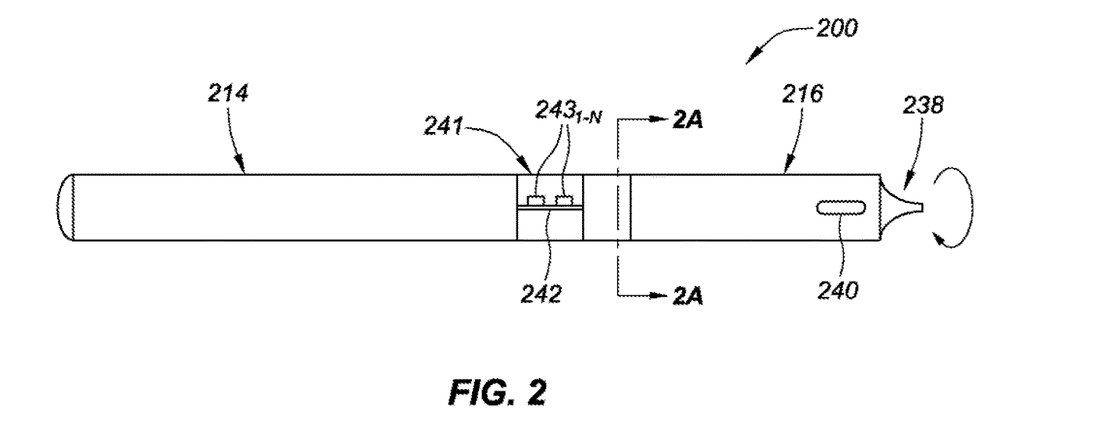
FIG. 2 is a side view of an e-cigarette, consistent with various embodiments of the present disclosure.

FIG. 2 is a side view of an e-cigarette 200, consistent with various embodiments of the present disclosure. The e-cigarette 200 includes a power supply portion 214 and an atomizer/liquid reservoir portion 216 which are removably coupled to one another to form the e-cigarette. In the present embodiment, the atomizer/liquid reservoir portion 216 includes a liquid level viewing window 240 which facilitates the user's determination of a remaining amount of e-cigarette liquid remaining in the liquid reservoir. The power supply portion 214 includes an indicator status window 241 which facilitates the user's viewing of indicator lights $243_{1-N}$ communicatively coupled to e-cigarette controller circuitry 242. In the present implementation, a user may grip an exterior of the power supply portion 214 and a nozzle 238 of the atomizer/liquid reservoir portion 216 may rotate freely relative to the power supply portion 214 to facilitate a user desired orientation of the nozzle. Moreover, when the e-cigarette is in use, a user's rotational inputs along a longitudinal axis of the e-cigarette will not affect the rotational alignment of the nozzle 238 relative to the user's mouth as the power supply portion 214 and the atomizer/liquid reservoir portion 216 may rotate independently of one another.

While power supply portion 214 and atomizer/liquid reservoir portion 216 are rotationally independent of one another along a longitudinal axis of the e-cig, controller circuitry 242 may freely rotate within the power supply portion, while maintaining rotational alignment with nozzle 238 of the atomizer/liquid reservoir portion. In such an embodiment, regardless of the relative, radial position of the nozzle to the power supply portion, indicator lights $243_{1-N}$ on the controller circuitry may be visible to a user. The indicator lights may visually indicate to a user various aspects about the e-cigarette's status (e.g., low battery, battery condition, low e-cigarette juice, error conditions, etc.).

While the embodiment of FIG. 2 has been presented with a relative rotational angle between electronic circuitry 242 and nozzle 238 locked, in other embodiments the nozzle may be rotatably adjustable relative to the electronic circuitry 242 (or vice versa).

Importantly, the embodiment of FIG. 2 facilitates a user's ability to adjust their grip on an exterior of the power supply portion 214 during a smoking session, and the nozzle 238 may rotate freely relative to the power supply portion to facilitate a user desired orientation of the nozzle relative to the user's mouth without the need to maintain a constant grip of the power supply portion to facilitate a desired orientation of the nozzle.

Figure 2A:
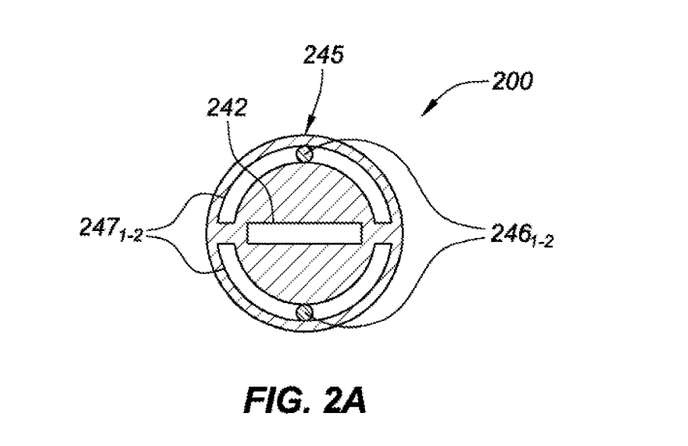
FIG. 2A is a cross-sectional front view of the e-cigarette of FIG. 2, consistent with various embodiments of the present disclosure.

FIG. 2A is a cross-sectional front view of the e-cigarette 200 of FIG. 2, consistent with various embodiments of the present disclosure. FIG. 2A shows a mechanical interface 245 which facilitates the relative rotation between the power supply portion 214 and atomizer/liquid reservoir portion 216. Importantly, the mechanical interface 245 limits a total angular rotation of the power supply portion relative to the reservoir portion. Limiting total angular rotation between the power supply portion relative to the reservoir portion may be necessary due to various lead wires which extend to/from the controller circuitry from other electronics (e.g., battery, heater coil, etc.) which have limited lead length and connectivity may be terminated if the lead wires are over extended. While a skilled artisan will appreciate that various implementations may achieve the desired relative rotation between the power supply portion 214 and atomizer/liquid reservoir portion 216 (while limiting a total angular rotation), FIG. 2A is directed to only one specific implementation. In FIG. 2A, runners $246_{1-2}$ are contained within tracks $247_{1-2}$ and facilitate rotational motion between the power supply portion 214 and atomizer/liquid reservoir portion 216. Each of the tracks extends approximately 180 degrees about a circumference of the power supply portion, limiting the total rotational offset between the power supply portion and the reservoir portion to 180 degrees (or 90 degrees in a clockwise direction and 90 degrees in a counter-clockwise direction). In other embodiments, the total rotational offset may be limited to a total of 90 degrees, or be as great as 360 degrees. While the present embodiment teaches two separate tracks, other embodiments may utilize a single track with two or more runners therein. In some embodiments, three or more runners may be desirable to facilitate improved structural integrity of the removable coupling between the power supply portion and the reservoir portion. The removable coupling may utilize various mechanical features well known to a skilled artisan. For example, the removable coupling may utilize one or more snap features.

Figure 3:
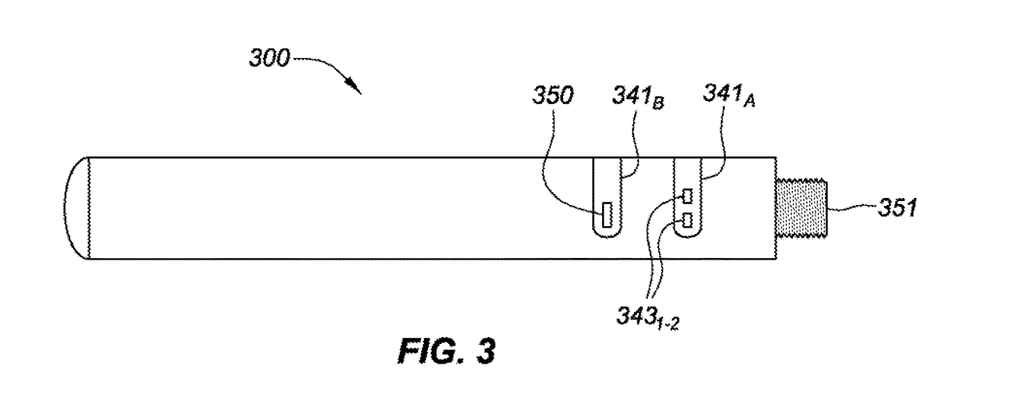
FIG. 3 is a top view of an e-cigarette, consistent with various embodiments of the present disclosure.

FIG. 3 is a top view of an e-cigarette power supply portion 300, consistent with various embodiments of the present disclosure. The power supply portion 300 of FIG. 3 includes a mechanical coupling 351 for coupling the power supply portion to an atomizer/liquid reservoir portion. The power supply portion 300 further includes a communication port 350 and one or more indicator lights $343_{1-2}$ which are accessible/visible via respective access windows $341_{A-B}$. When coupled to the atomizer/liquid reservoir portion, the atomizer/liquid reservoir portion, the communication port, and the indicator lights are radially coupled to one another. That is, rotation of the atomizer/liquid reservoir portion along a longitudinal axis of the e-cigarette causes reciprocal rotation of the communication port and indicator lights. The user's ability to customize the relative locations of the communication port and indicator lights on the power supply portion 300 may be desirable for a number of reasons. For example, improved visibility of the indicator lights during use and/or while charging. Also, in certain applications the communication port (which may be used for charging of the e-cigarette) may not be accessible. The ability to rotate the communication port about the power supply portion may alleviate the restricted access.

Figure 4:
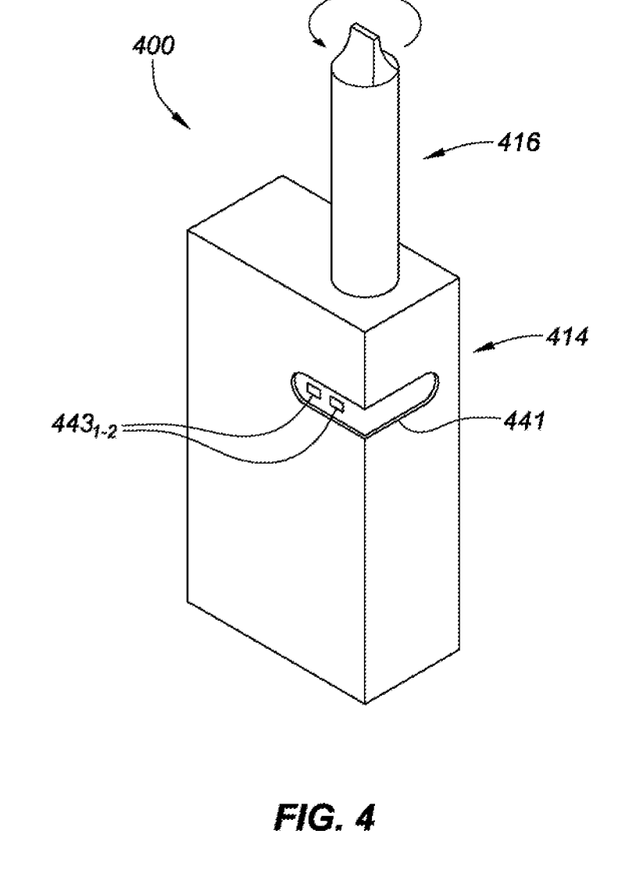
FIG. 4 is an isometric front view of an e-cigarette, consistent with various embodiments of the present disclosure.

FIG. 4 is an isometric front view of an e-cigarette 400, consistent with various embodiments of the present disclosure. The e-cigarette of FIG. 4 includes a power supply portion 414 and an atomizer/liquid reservoir portion 416. The reservoir portion is rotatably coupled to the power supply portion. The power supply portion includes an access window 441 that facilities a user's viewing of indicator lights $443_{1-2}$ below the access window. The access window may extend across two or more sides of the power supply portion 414 of the e-cigarette 400. In response to a rotation of the reservoir portion 416, an electronic circuit board including the indicator lights $443_{1-2}$ rotates in kind. In such an embodiment, the indicator lights $443_{1-2}$ are always readily visible to a user during operation of the e-cigarette, regardless of the orientation in which the user prefers to hold the e-cigarette.

Figure 5:
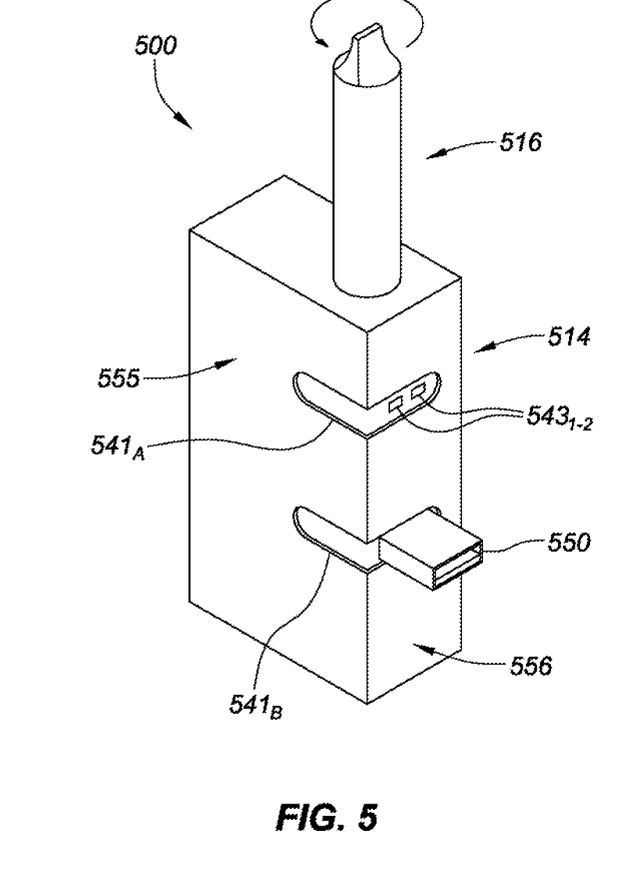
FIG. 5 is an isometric front view of an e-cigarette, consistent with various embodiments of the present disclosure.

FIG. 5 is an isometric front view of an e-cigarette 500, consistent with various embodiments of the present disclosure. The e-cigarette of FIG. 5 includes a power supply portion 514 and an atomizer/liquid reservoir portion 516. The reservoir portion is rotatably coupled to the power supply portion. The power supply portion includes an access window $541_A$ that facilities a user's viewing of indicator lights $543_{1-2}$ below the access window. The access window may extend across two or more sides of the power supply portion 514 of the e-cigarette 500. In response to a rotation of the reservoir portion 516, an electronic circuit board including the indicator lights $543_{1-2}$ rotates in kind. In such an embodiment, the indicator lights $543_{1-2}$ are always readily visible to a user during operation of the e-cigarette, regardless of the orientation in which the user prefers to hold the e-cigarette.

Further in regards to the embodiment presented in FIG. 5, the power supply portion 514 may further include a second access window $541_B$ that facilitates a communication port 550 to extend out of the power supply portion and facilitate coupling thereto. The communication port may be used for programming the e-cigarette, and/or charging. Due to space limitations, the communication port may not be able to access external communication ports. As shown in FIG. 5, the communication port may be manipulated to rotate approximately 90 degrees (from a first face 555 to a second face 556). In the present embodiment, the second face of the power supply portion is narrower, facilitating coupling to a communication port with width dimensional constraints.

In FIG. 5, communication port 550 may be manually manipulated by the user via a direct force on the communication port that induces the rotation. Alternatively, or in addition, rotation of the reservoir portion 516 may cause a reciprocal rotation of the communication port 550. The communication port 550, in such an embodiment, may be coupled to a pivoting axis that is directly and/or indirectly coupled to the reservoir portion. In some more specific implementations of the embodiment of FIG. 5, the indicator lights 543$_{1-2}$ may rotate in response to the user inputs on the reservoir portion 516, and the communication port 550 may rotate in response to a direct force exerted on the communication port itself.

Aspects of the present disclosure are directed to an electronic smoking device including a power supply portion, and an atomizer/liquid reservoir portion. The atomizer/liquid reservoir portion is removeably coupled to the power supply portion. The atomizer/liquid reservoir portion may freely rotate about a longitudinal axis of the electronic smoking device, relative to the power supply portion. In some implementations, the atomizer/liquid reservoir portion may freely rotate about the longitudinal axis in response to a user input. The power supply portion may include, in some embodiments, controller circuitry with indicator lights. The controller circuitry is rotatably coupled to the atomizer/liquid reservoir portion, and rotates in response to a rotational input on the atomizer/liquid reservoir portion. The controller circuitry may further facilitate maintained visibility of the indicator lights by a user following the rotational input on the atomizer/liquid reservoir portion. In yet further more specific embodiments, the power supply portion further includes a communication port communicatively coupled to the controller circuitry. The communication port is rotatable about the longitudinal axis in response to the rotational input on the atomizer/liquid reservoir portion.

In some implementations of an electronic smoking device, the atomizer/liquid reservoir portion includes a nozzle, and the atomizer/liquid reservoir portion facilitates rotational alignment between the nozzle and a mouth of a user. The rotation of the atomizer/liquid reservoir portion, relative to the power supply portion, may be limited to a range between 90 and 180 degrees.

Various embodiments of the present disclosure are directed to a power supply portion of an electronic cigarette including a housing, a power supply situated within the housing, and controller circuitry situated within the housing and electrically coupled to the power supply. The controller circuitry rotates, about a longitudinal axis, relative to the housing in response to a rotational input on an atomizer/liquid reservoir portion when coupled to the power supply portion. In some implementations, the housing includes a transparent window, the controller circuitry includes one or more indicator lights, and the controller circuitry facilitates maintained visibility of the indicator lights by rotating in response to the rotational input of the atomizer/liquid reservoir portion. In yet other implementations, the controller circuitry, in response to the rotational input on the atomizer/liquid reservoir portion rotatably coupled to the power supply portion, facilitates maintained user visibility of the indicator lights through the transparent window by rotating.

The power supply portion may further include a communication port communicatively coupled to the controller circuitry and which rotates with the controller circuitry about the longitudinal axis. In various implementations of the power supply portion discussed above, the rotation of the controller circuitry, relative to the housing, may be limited to 90 degrees.

Aspects of the present disclosure are also directed to methods of reconfiguring an electronic cigarette. The method including: applying a torque along a longitudinal axis of an atomizer/liquid reservoir portion of the electronic cigarette, translating the torque on the atomizer/liquid reservoir portion to controller circuitry housed within a power supply portion of the electronic cigarette, the controller circuitry rotatably coupled to the atomizer/liquid reservoir portion, and rotating the controller circuitry, in response to the translated torque on the controller circuitry. The step of rotating the controller circuitry may maintain user visibility of indicator lights on the controller circuitry. The indicator lights may be visible through a transparent window in the power supply portion that extends at least partially about a circumference of the power supply portion. In various implementations, the step of rotating the controller circuitry maintains rotational alignment of a communication port communicatively coupled to the controller circuitry and the atomizer/liquid reservoir portion. The method may further include limiting the rotation of the controller circuitry by discontinuing the translation of torque onto the controller circuitry once the rotation of the controller circuitry reaches 90 degrees.

Some method of reconfiguring an electronic cigarette, consistent with the present disclosure, may further include the step of rotating a communication port about the longitudinal axis. The communication port extending out of a window in the power supply portion which extends at least partially about a circumference of the power supply portion.

While this invention has been described in connection with what is presently considered to be one example embodiment, it is to be understood that the invention is not limited to the disclosed embodiments, but, on the contrary, is intended to cover various modifications and equivalent arrangements included within the scope of the appended claims. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various modules or other circuits may be implemented to carry out one or more of the operations and activities described herein and/or shown in the figures. In these contexts, a "module" is a circuit that carries out one or more of these or related operations/activities (e.g., controller circuitry). For example, in certain of the above-discussed embodiments, one or more modules are discrete logic circuits or programmable logic circuits configured and arranged for implementing these operations/activities. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/activities.

LIST OF REFERENCE SIGNS

| 10 | electronic smoking device |
| 12 | end cap |
| 14 | power supply portion |
| 16 | atomizer/liquid reservoir portion |
| 18 | light-emitting diode (LED) |
| 20 | air inlets |
| 22 | battery |
| 24 | control electronics |
| 26 | airflow sensor |
| 28 | atomizer |
| 30 | heating coil |

-continued

| 32 | wick |
| 34 | central passage |
| 36 | liquid reservoir |
| 38 | air inhalation port |
| 200 | e-cigarette |
| 214 | power supply portion |
| 216 | atomizer/liquid reservoir portion |
| 238 | nozzle |
| 240 | liquid level viewing window |
| 241 | indicator status window |
| 242 | e-cigarette controller circuitry |
| 243 | light emitting diodes |
| 245 | mechanical interface |
| 246 | runners |
| 247 | tracks |
| 300 | power supply portion |
| 341 | indicator status window |
| 343 | light emitting diodes |
| 350 | communication port |
| 351 | mechanical coupling |
| 400 | e-cigarette |
| 414 | power supply portion |
| 416 | atomizer/liquid reservoir portion |
| 441 | indicator status window |
| 443 | light emitting diodes |
| 500 | e-cigarette |
| 514 | power supply portion |
| 516 | atomizer/liquid reservoir portion |
| 541 | indicator status window |
| 543 | light emitting diodes |
| 550 | communication port |
| 555 | first face |
| 556 | second face |

What is claimed is:

1. An electronic smoking device comprising:
a power supply portion, wherein the power supply portion includes controller circuitry with indicator lights; and
an atomizer/liquid reservoir portion removably coupled to the power supply portion, wherein:
an entirety of the atomizer/liquid reservoir portion is configured and arranged to freely rotate about a longitudinal axis of the electronic smoking device, relative to the power supply portion, in response to a user input,
the rotation of the atomizer/liquid reservoir portion relative to the power supply portion is limited to a particular amount of rotation; and
the controller circuitry is rotatably coupled to the atomizer/liquid reservoir portion, and the controller circuitry is configured and arranged to rotate in response to a rotational input on the atomizer/liquid reservoir portion while the remainder of the power supply portion is static.

2. The electronic smoking device of claim 1, wherein the atomizer/liquid reservoir portion includes a nozzle, and the atomizer/liquid reservoir portion is further configured and arranged to facilitate rotational alignment between the nozzle and a mouth of a user by being independently rotatable relative to the power supply portion.

3. The electronic smoking device of claim 1, wherein the atomizer/liquid reservoir portion includes a nozzle with a first primary plane that is positioned orthogonal to a second primary plane of the indicator lights, and the nozzle and the indicator lights are rotatably coupled to maintain axial alignment along a longitudinal axis of the electronic smoking device in response to the rotational input on the atomizer/liquid reservoir portion.

4. The electronic smoking device of claim 1, wherein the power supply portion further includes a communication port communicatively coupled to the controller circuitry, the communication port rotatably coupled to the atomizer/liquid reservoir portion and configured and arranged to rotate about the longitudinal axis in response to the rotational input on the atomizer/liquid reservoir portion.

5. The electronic smoking device of claim 1, wherein the rotation of the atomizer/liquid reservoir portion, relative to the power supply portion, is limited to 90 degrees.

6. The electronic smoking device of claim 1, wherein the rotation of the atomizer/liquid reservoir portion, relative to the power supply portion, is limited to 180 degrees.

7. The electronic smoking device of claim 1, further including a mechanical interface configured and arranged to facilitate the relative rotation between the power supply portion and atomizer/liquid reservoir portion and to limit a total angular rotation of the power supply portion relative to the atomizer/liquid reservoir portion.

8. The electronic smoking device of claim 7, the mechanical interface including one or more runners contained within one or more tracks, the runners and tracks configured and arranged to facilitate rotational motion between the power supply portion and atomizer/liquid reservoir portion.

9. The electronic smoking device of claim 8, wherein each of the tracks extends approximately 180 degrees about a circumference of the power supply portion, thereby limiting the total rotational offset between the power supply portion and the atomizer/liquid reservoir portion to 180 degrees.

10. The electronic smoking device of claim 8, wherein each of the tracks extends approximately 90 degrees about a circumference of the power supply portion, thereby limiting the total rotational offset between the power supply portion and the atomizer/liquid reservoir portion to 90 degrees.

11. An electronic smoking device comprising:
 a power supply portion including a housing, a power supply situated within the housing, and controller circuitry situated within the housing and electrically coupled to the power supply, the controller circuitry configured and arranged to rotate, about a longitudinal axis, relative to the housing in response to a rotational input on an atomizer/liquid reservoir portion when coupled to the power supply portion, wherein the controller circuitry further includes a communication port configured and arranged to rotate about the longitudinal axis; and
 an atomizer/liquid reservoir portion removably coupled to the power supply portion;
 wherein the atomizer/liquid reservoir portion is configured and arranged to rotate about a longitudinal axis of the electronic smoking device by an amount less than a full rotation, relative to the power supply portion.

12. The electronic smoking device of claim 11, wherein the housing includes a transparent window, the controller circuitry includes one or more indicator lights, and the controller circuitry is further configured and arranged to facilitate maintained visibility of the indicator lights by rotating in response to the rotational input of the atomizer/liquid reservoir portion.

13. The electronic smoking device of claim 11, wherein the power supply portion further includes one or more indicator lights configured and arranged to be visible through a transparent window in the housing that extends at least partially about a circumference of the housing.

14. The electronic smoking device of claim 11, wherein the communication port extends out of a window in the housing of the power supply portion, wherein the window extends at least partially about a circumference of the housing.

15. An electronic smoking device comprising:
 a power supply portion including a housing, a power supply situated within the housing, and controller circuitry situated within the housing and electrically coupled to the power supply, the controller circuitry configured and arranged to rotate, about a longitudinal axis, relative to the housing in response to a rotational input on an atomizer/liquid reservoir portion when coupled to the power supply portion, wherein the controller circuitry further includes a communication port configured and arranged to rotate about the longitudinal axis, the communication port extending out of a window in the housing of the power supply portion which extends at least partially about a circumference of the housing; and
 an atomizer/liquid reservoir portion removably coupled to the power supply portion;
 wherein the atomizer/liquid reservoir portion is configured and arranged to rotate about a longitudinal axis of the electronic smoking device by an amount less than a full rotation, relative to the power supply portion.

* * * * *